United States Patent [19]

Lewin

[11] 4,197,855

[45] Apr. 15, 1980

[54] DEVICE FOR MEASURING THE LOCATION, THE ATTITUDE AND/OR THE CHANGE IN LOCATION OR, RESPECTIVELY, ATTITUDE OF A RIGID BODY IN SPACE

[75] Inventor: Arthur Lewin, Johannesburg, South Africa

[73] Assignee: Siemens Aktiengesellschaft, Berlin & Munich, Fed. Rep. of Germany

[21] Appl. No.: 887,654

[22] Filed: Mar. 17, 1978

[30] Foreign Application Priority Data

Apr. 4, 1977 [DE] Fed. Rep. of Germany ....... 2715106

[51] Int. Cl.$^2$ ......................... A61B 5/05; A61B 5/06; A61B 5/10
[52] U.S. Cl. ................................... 128/653; 128/665; 128/777; 128/782
[58] Field of Search ............... 128/2 S, 2 N, 2 R, 653, 128/665, 777, 782, 774, 776, 731, 1.3; 32/19-21, DIG. 6; 324/207, 208; 340/686

[56] References Cited

U.S. PATENT DOCUMENTS

| 3,439,358 | 4/1969 | Salmons | 128/2 S |
| 3,528,402 | 9/1970 | Abramowitz | 128/2 R |
| 3,822,694 | 7/1974 | Mills | 128/2 S |

FOREIGN PATENT DOCUMENTS

| 1013880 | 6/1960 | Fed. Rep. of Germany | |
| 182854 | 8/1966 | U.S.S.R. | 128/2 S |
| 232447 | 4/1969 | U.S.S.R. | 128/2 S |

Primary Examiner—Robert W. Michell
Assistant Examiner—Jeffrey W. Tayon
Attorney, Agent, or Firm—Hill, Van Santen, Steadman, Chiara & Simpson

[57] ABSTRACT

In the illustrated embodiment, a field generator may be arranged on the body or at an interval therefrom, and produces a defined irregular field. For detecting the field flux a first surface with a plurality of sensor elements is provided, at least a part of which is distributed in two lines running parallel to each other and coupled electrically differentially together. At an interval from the first surface there is provided a second surface, parallel thereto, with further, correspondingly arranged sensor lines. The sensor lines of both surfaces run parallel to one another; the differential signals of the line pair of the first surface are electrically differentially linked to the differential signals of the line pair of the second surface. The device is in particular intended for measuring the location, the attitude and/or the change in location or, respectively, attitude of the jaw or of a tooth of a patient. Thus information may be provided with respect to three degrees of freedom of both translational and rotational movement.

18 Claims, 6 Drawing Figures

DEVICE FOR MEASURING THE LOCATION, THE ATTITUDE AND/OR THE CHANGE IN LOCATION OR, RESPECTIVELY, ATTITUDE OF A RIGID BODY IN SPACE

BACKGROUND OF THE INVENTION

The invention relates to a device for measuring and registering the location, the attitude and/or the change in location or, respectively, attitude of a rigid body in space, using a field generator arranged directly on the body or at an interval therefrom, preferably a magnetic-field generator; with means arranged at an interval from the field generator, and independent of the body, for detecting the field flux or, respectively, the field flux alteration during a measurement; and an electronic device for obtaining and evaluating electrical signals originating in conjunction with a field flux, or respectively, a field flux change.

Known measurement devices of this kind (German Pat. No. 1,013,880, U.S. Pat. No. 3,822,694) are either not suitable for measuring the attitude or, respectively, an attitudinal change of the body in space or it is not possible to measure a rotational movement with them, but rather only a mixture of rotational and translational movement.

SUMMARY OF THE INVENTION

The goal of the invention is to provide a measurement device of the type named at the outset, which is improved in comparison to the prior art, and with which, in addition to measuring the location of the body in space, it is also possible to measure the attitude and/or a change in the location or, respectively, attitude of the body in space, in which regard it must be taken into consideration that, in addition to the three degrees of freedom for a translational movement, the three degrees of freedom of a rotational movement are also measured.

This goal is achieved, in a device of the type named at the outset, in that the field generator is constructed in such a way that it produces a defined, irregular field, and that, for detecting the field flux, at least one first surface, preferably three first surfaces in planes perpendicular to one another, is present with a plurality of sensor elements, at least a part of which are distributed in two lines running parallel to each other, with the two sensor lines of the first surface being electrically differentially coupled together, and that at an interval from the first surface a second surface parallel thereto is provided having further, correspondingly arranged sensor lines, and that the sensor lines of both surfaces run parallel to each other and that the differential signals of the line pair of the first surface are electrically differentially linked to the differential signals of the line pair of the second surface.

Advantageous further developments and refinements are indicated in the sub-claims.

The inventive device can be utilized for all conceivable measurement operations in which, in addition to measuring the location the objective is to measure the attitude and/or a change in the location or, respectively, attitude of a rigid body in space. Utilization in the field of medicine is to be particularly emphasized, for example in sports medicine or orthopedics, where, for certain diagnostic purposes, it is desired, for example, to determine the attitude or, respectively, an attitudinal change of the bones in certain movement procedures. The sample embodiment of the invention explained below with the aid of the drawing shows the utilizaton of the inventive device in dentistry, where it is desired to determine the precise attitude, or, respectively, an attitudinal change of the lower jaw.

For certain applications it is advantageous to attach the field generator to the rigid body to be measured, and to adjacently arrange the means for detecting the field flux independently thereof in space; in principle, however, it is conceivable to provide a reverse of the arrangement, in such a way that the field flux measurement device is arranged on the rigid body, and the field generator in space. As a field generator it is possible to utilize a permanent magnet, an electromagnetic field generator, or also a light source, depending on the application for which the inventive device is to be employed.

A sample embodiment of the invention is explained more specifically with the aid of the accompanying sheets of drawings; other objects, features and advantages will be apparent from this detailed disclosure and from the appended claims.

DETAILED DESCRIPTION

Figure 1:
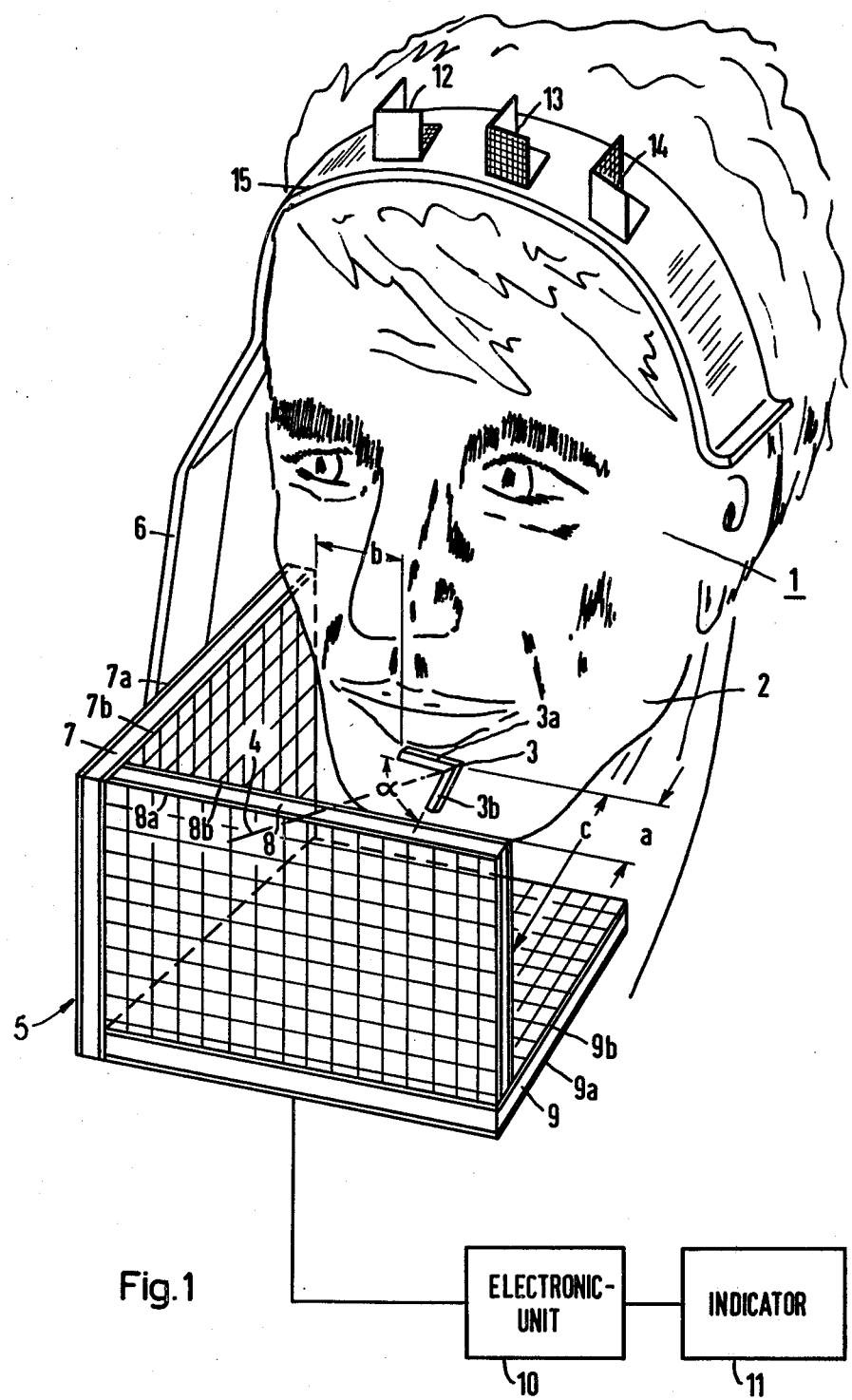
FIG. 1 is a somewhat diagrammatic perspective view illustrating a measurement system in accordance with the present invention as utilized in the field of dentistry.

FIG. 1 shows, in schematic representation, the inventive measurement system as utilized in the field of dentistry for determining the location, the attitude and/or a change in the location or, respectively, attitude of the lower jaw of a patient. The patient's head is designated with 1; the lower jaw with 2. A permanent magnet serving as field generator is designated with 3, which is attached intraorally at any desired point of the lower jaw. The attachment can be done, for example, by means of adhesives or cements (impression masses). The magnetic field generator 3 consists of two identically dimensioned bar magnets 3a, 3b, which are arranged at an angle $\alpha < 180°$ to each other. For the sake of better recognition the magnetic field generator 3 is represented substantially enlarged; in a preferable embodiment the bar magnets each have a length of three mm and a cross section of one mm square (1 mm $\times$ 1 mm). The angle bisector of the two bar magnets 3a, 3b is designated with 4.

Extraorally there is disposed an arrangement, designated with 5, of several surfaces extending perpendicular to one another, with magnetic field sensors, which said arrangement is mounted on the patient's cranium via a mounting 6. The arrangement 5 thus remains locationally fixed vis-a-vis the lower jaw so as to provide a reference position as the latter is moved relative to the cranium.

The arrangement 5 consists of three double plates 7, 8 and 9 arranged perpendicularly to one another, each of which consists of two plane surface elements arranged parallel to each other, with the outer surface element being designated in each case with the index "a", and the inner surface element facing the patient's head being designated in each case with the index "b". The arrangement of the double plates 7, 8 and 9 is such that the surface element 7 is situated laterally to the patient's head, with the angle bisector 4 of the opening angle $\alpha$ of the magnetic field generator 3 running approximately through the edge intersection region of the two double plates 7 and 8.

Double plates 7 to 9 carry, as will be more specifically explained later, a plurality of sensor elements which pick up the magnetic flux of the magnetic field generator 3. Their outputs are connected to an electronic unit, designated with 10, which has the task of detecting and analyzing the signals responsive to the magnetic fluxes or, respectively, magnetic flux changes and passing them along to a subsequently connected indicator 11 in the form of evaluatable signals.

The reference numerals 12, 13 and 14 designate sensor elements attached to a carrier member 15 rigidly connected to the mounting bracket 6, which sensor elements are aligned parallel to surface elements 7, 8 and 9 and which serve to compensate the earth's magnetic field. The sensor surfaces are shown crosshatched. A movement of the lower jaw 2 can, as with any other rigid body which is moved in space, be composed of rotational and translational movements. With the represented arrangement of the double plates, which are respectively equipped with sensor elements, as will be explained more specifically later, it is possible to measure not only the three degrees of freedom of the translational movement but also the three degrees of freedom of the rotational movement, and thus to measure every attitude or, respectively, attitudinal change of a point on the jaw in space.

Figure 2:
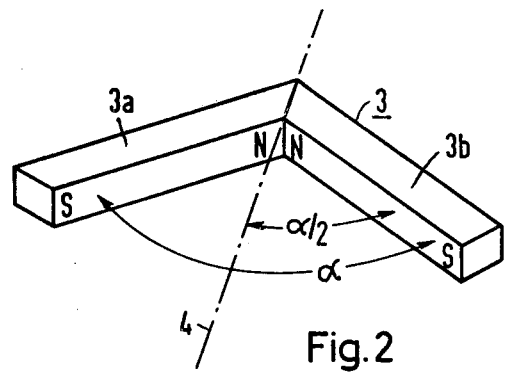
FIG. 2 is a somewhat diagrammatic enlarged perspective view of the field generator utilized in the embodiment of FIG. 1.

FIG. 2 shows the magnetic field generator 3 in diagrammatic and greatly enlarged representation. It is formed of two bar magnets 3a, 3b, arranged at an angle $\alpha$ of about 130° to each other, which said bar magnets butt against each other at their like poles (N—N). The thus executed arrangement of the bar magnets produces an irregular magnetic field, whose field strength is varyingly large in planes which are perpendicular to each other. In contrast to a symmetrical magnetic field, it is possible with this asymmetrical magnetic field to determine all degrees of freedom of a rotational movement, because it is rotation-asymmetrical in all dimensions.

Figure 3:
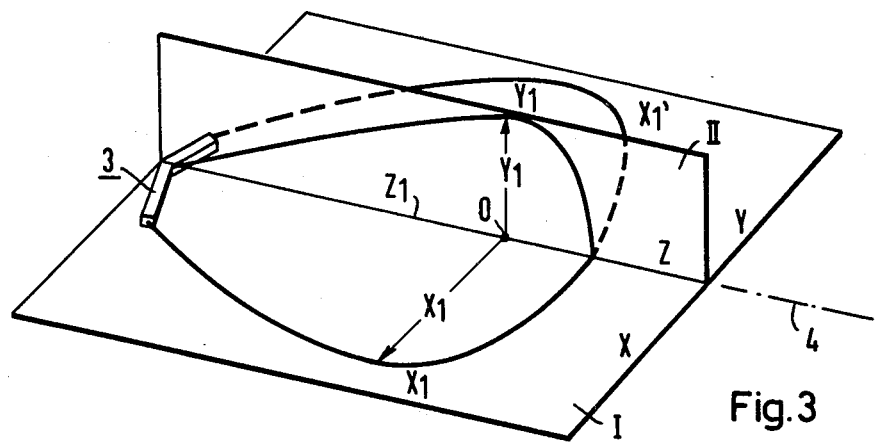
FIG. 3 is a diagrammatic perspective view illustrating the irregular field produced by the field generator of FIGS. 1 and 2.

FIG. 3 shows the path of the lines of force of the magnetic field generator 3 in two planes I and II which are perpendicular to each other. It follows from the representation that, viewed from a point O, varyingly large field strengths x1, y1 and z1 are present in the three directions x, y and z. What is involved here is therefore an irregular three-dimensional magnetic field.

In order to be able to exactly determine the magnetic field in a plane, the arrangement of an infinite number of magnetic flux sensors in a plane is theoretically necessary. In practice, however, only that number of sensor elements is required which depends on the resolving power of the individual sensor element in order to be able to sufficiently exactly determine a movement in a prescribed plane. With a single sensor element, however, the movement of a magnetic field in a flat plane cannot be determined.

Figure 4:
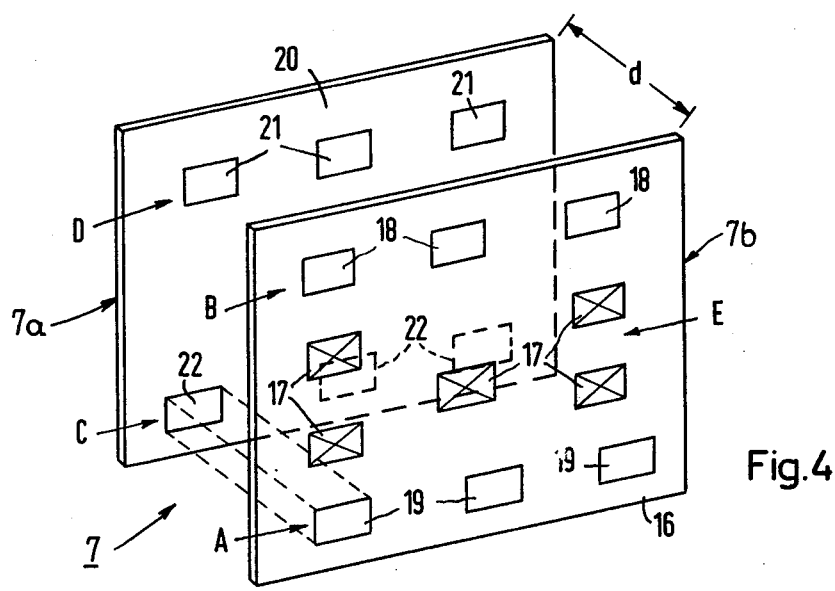
FIG. 4 is a diagrammatic perspective view showing details of construction applicable to each of the double plate assemblies of FIG. 1.

Using the example of a sensor surface (for example, 7 in FIG. 1) FIG. 4 shows the structure of the double plates with the arrangement of the sensor elements which measure the magnetic flux emanating from the field generator 3 or, respectively, the flux change.

Double plate section 7 consists of an outer surface element 7a and an inner surface element 7b. The inner surface element 7b is formed from a ceramic or a synthetic material plate 16, on which a first group of sensor elements (Hall generators) 17 is arranged, preferably distributed uniformly, and above and below them one row each of further sensor elements 18 and 19. The Hall generators are cemented onto the synthetic material or ceramic plate 16 in the form of platelets and, in order to enlarge the receiving surface of each sensor element, are covered with a low-remanence, ferromagnetic material, for example mumetal. The group of the preferably uniformly distributed sensor elements 17 forms a sensor surface E; the sensor elements 18 and 19 respectively form sensor lines A and B. The surface element 7a, arranged at an interval d from the inner surface element 7b, also consists of a ceramic or synthetic material plate 20, on which two further sensor lines C and D with sensor elements 21 and 22 are arranged precisely flush and parallel to the sensor lines A and B of plate 7b, and parallel with each other.

Each of the double plates 7, 8, 9 is preferably equipped with the same number of sensor elements and in the same arrangement as described in FIG. 4. Sensor lines A and B of the inner surface elements and those of the outer surface elements (C and D) are in each case coupled differentially with each other, i.e. they each emit a differential signal at the point.

The possibility exists of measuring the translation only with the sensor lines, i.e. without elements E, if the lines such as A and B of the first planes are not differentially coupled, but rather additively coupled. The signals delivered from lines A and B would thus be used once differentially (to measure rotation) and once additively (to measure translation) using differential-sum amplifiers.

Every movement of the magnetic field generator in the three degrees of freedom x, y, and z can be measured, in a pure translational movement, with the sensor surface E, which is formed by the sensor elements 17. It is fundamentally possible to expand the measurement range and to measure any rotational angles whatever—even greater than 180°—if either the measurement arrangement is selected large enough (extended), or a similar measurement arrangement is additionally used or, respectively, parts of the measurement arrangement are present in duplicate (for example right and left, above and below, in front of and behind the patient's head). The parts of the measurement arrangement must only be present at the place to which the magnetic field is directed during the movement to be measured. Sensor lines or linear arrays A through D, which are differentially coupled together, serve for a determination of the rotational movement, as well. If the sensor surfaces E arranged on the inner surface elements 7b, 8b, and 9b (which are respectively perpendicular to one another), are situated at the beginning of a measurement, at a known distance a, b, and c (FIG. 1) with regard to the magnetic field generator 3, then every movement of the field generator relative to the three planes is known. If there is no rotational movement, then the movement of the field, as it is measured by the three sensor surfaces, is a function of the movement of the field generator. However, if a translational and a rotational movement occur simultaneously, which is the case as a rule, then the movement, as it is measured by the three sensor surfaces E, consists of a pure translation and a translation which is caused by rotation.

Sensor lines A to D serve to determine the rotational movement. Respectively, two sensor lines A, B and C, D are arranged opposite each other on a plane, and the two lines are electrically differentially coupled together. As a result the movement of a magnetic field between the two lines is measured as a differential. Presupposing that the magnetic field generator is situated at a specific distance from a plane and rotates around its midpoint in such a way that the rotational axis lies parallel to this plane, which carries the differentially arranged sensor elements, then the output signal of the sensor elements is a direct function of the rotation, taking into consideration an alteration in the field strength, by reason of the attitudinal change of the magnetic field generator in space.

Since the sensor lines (A and B) and sensor surfaces (E) on the inner surface elements 7b, 8b, 9b lie in the same plane, rotation and translation can be simultaneously measured in one plane.

In order to measure the rotation of the magnetic field about any axis, the further sensor lines C and D which are arranged at an interval "d" (FIG. 4) from the sensor lines arranged on the inner surface elements are needed. The important thing is that the sensor lines C and D are parallel to the sensor lines A and B.

If the differential signals of the two sensor line pairs (A, B and C, D) are differentially coupled together, then a resulting signal is obtained which consists only of the portion of the rotation of the magnetic field.

Figure 5:
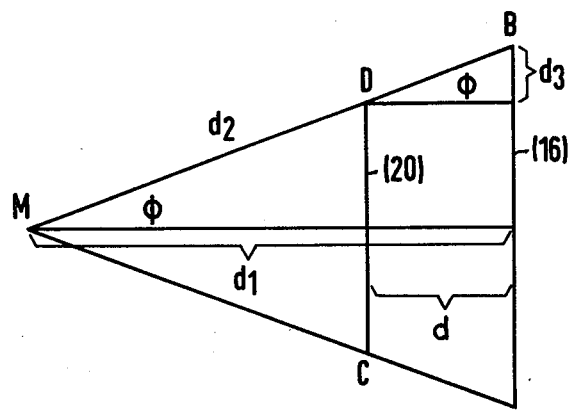
FIG. 5 is a diagram indicating by means of lines AB and CD, the arrangement of the plates of FIG. 4, and indicating the manner in which a linear measure for pure translation may be obtained.
Figure 6:
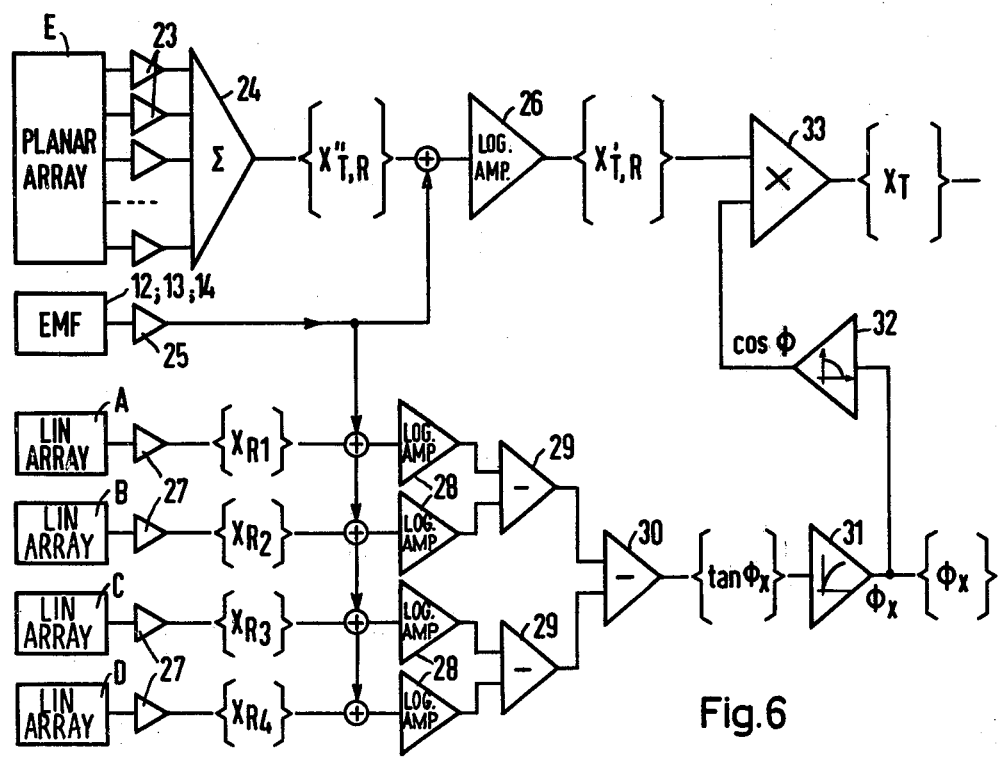
FIG. 6 is a circuit diagram illustrating the manner in which a signal representing pure translation, and a signal representing rotational angle may be obtained using the double plate arrangement of FIG. 4.

The principle of the signal processing is explained more specifically with the aid of FIGS. 5 and 6, with only one allied pair of freedom degrees (x) and associated rotational angle $\phi_x$ being illustrated in these explanations. For the remaining degrees of freedom (y, angle $\phi_y$, z, angle $\phi_z$) the corresponding is true.

In FIG. 6 the arrangement of the sensor surface or planar array for the measurement of translational movement in accordance with the representation in FIG. 4 is designated with E, with A, B C and D designating the sensor lines or linear arrays for the measurement of a rotational movement, and with 12; 13; 14 designating the sensor elements for compensating the earth's magnetic field (EMF). The signals obtained from the sensor elements of sensor surface E are initially fed, via preamplifiers 23 to a summer 24, whose output signal $x''_{T,R}$ (T = translation; R = rotation) is a measure for the translation and for a translation produced by rotation. The signals from the sensor elements 12 through 14 are amplified by a preamplifier 25. Subsequently the amplified signal is added to the $x''_{T,R}$ signal, and the mixed signal is fed to a logarithmic amplifier 26, at whose output a linearized signal $x'_{T,R}$ is emitted which is free of components due to the earth's magnetic field.

Via preamplifiers 27 and after compensation of the earth's magnetic field with the aid of sensor elements 12 to 14, the signals from the sensor arrays A to D are also fed to logarithmic amplifiers 28 for linearization. By means of differential amplifiers 29 a differential signal is achieved in each case between sensor arrays A and B or, respectively, C and D. From the two output signals of the differential amplifiers 29 the difference is again formed in the differential member 30. At the output of the differential member 30 a tan $\phi_x$ signal is obtained, which is a linear measure for the tangent of the rotational angle $\phi_x$. This output signal is only influenced by the rotation. With the aid of a tan $\phi_x$ to $\phi_x$ converter 31 the rotational angle $\phi_x$ can be determined. At the output of the converter 31 the rotational angle $\phi_x$ for the freedom degree x is thus obtained directly.

A correction of the translational signal ($x'_{T,R}$), which is present at the output of the logarithmic amplifier 26, is done with aid of a $\phi_x$ to cos $\phi_x$ converter 32, with which the angle $\phi_x$ is converted into a corresponding cosine signal. This cosine signal is multiplied with the output signal of the logarithmic amplifier 26 in a multiplier 33. At the output of the multiplier 33 the true distance $x_T$ is obtained, which is a linear measure for a pure translation in the x direction.

Referring to FIG. 5, the following equation is valid: $d_1/d_2 = \cos \phi$; $a_1 = d_2 \cos \phi$ (compare FIG. 5).

The circuit according to FIG. 6 takes this equation into account.

FIG. 4 may be taken as illustrating a low-remanence ferromagnetic layer (of mumetal or the like) overlying each of the magnetic flux sensitive elements since the two components may have identical area and since the magnetic layer may be directly superimposed over a Hall effect layer, for example, as viewed in FIG. 4, to define each of the sensor elements 17–22.

By way of example, angle bisector 4, FIGS. 1 and 2, may extend through the common point of intersection of the three median planes defined by the three pairs of plates, 7, 8 and 9, FIG. 1.

In the illustrated embodiment each pair of panels such as 16, 20, FIG. 4, has a separation d which is sufficiently small in relation to the relevant portion of the irregular field configuration so that the differential signal from amplifier 30 is substantially independent of translational components in the movement of field source 3, over the range of movement to be measured.

It will be apparent that many modifications and variations may be effected without departing from the scope of the novel concepts and teachings of the present invention.

I claim as my invention:

1. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux reponsive means for obtaining and evaluating the electrical signals from the flux responsive means, characterized in said field generator being constructed such that it produces a defined irregular field, and said flux responsive means comprising at least one first surface, said first surface having a plurality of sensor elements, at least a part of which are arranged to form first sensor lines running parallel to each other, the sensor elements of the respective first sensor lines providing respective outputs and such respective outputs being electrically differentially coupled together for supplying a first differential signal, and comprising at least one second surface disposed between the field generator and the first surface, and parallel to the first surface to form a pair therewith and at an interval therefrom, the second surface having a plurality of second sensor lines comprising series of sensor elements extending parallel to respective sensor lines of the first surface, with the sensor elements of the respective second sensor lines of the second surface providing respective outputs and such outputs being electrically differentially coupled together for supplying a second differential signal, and said electronic device having means for differentially combining the first and second differential signals with respect to the first and second surfaces of said pair, said field generator comprising means for producing a magnetic field of irregular field configuration such that the output from said last mentioned means is responsive to relative rotation of said field generator while being relatively insensitive to translational components of movement of the field generator over a range of movement to be measured.

2. A system according to claim 1, characterized in one of said first and second surface additionally having a sensor array comprising a plurality of further sensor elements for supplying further signals in accordance with field flux from the field generator, the electronic device having means for additively combining said further signals with respect to said sensor array.

3. A system according to claim 2, characterized in the further sensor elements being arranged between respective sensor lines of said one surface.

4. A system according to claim 1, 2 or 3, characterized in said pair of said first and second surface (e.g. 7a, 7b) comprising a respective pair of first and second plane carrier sections (16, 20) situated opposite and parallel to each other at an interval (d) and mounting the respective first and second sensor lines (A, B; C, D) in such a way that respective ones of the first and second sensor lines (A, C; B, D) of each of the respective pairs of carrier sections (16, 20) are arranged parallel to one another.

5. A system according to claim 1, 2 or 3, characterized in said flux responsive means comprising three pairs of said first and second surfaces (7a, 7b; 8a, 8b; 9a, 9b) arranged in planes perpendicular to one another.

6. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux responsive means for obtaining and evaluating the electrical signals from the flux responsive means, characterized in said field generator (3) being constructed such that it produces a defined irregular field, and said flux responsive means comprising at least one first surface, said first surface having a plurality of sensor elements (17, 18, 19), at least a part of which (18, 19) are arranged to form first sensor lines (A, B) running parallel to each other, the sensor elements of the respective first sensor lines being electrically differentially coupled together for supplying a first differential signal, and comprising at least one second surface disposed parallel to the first surface to form a pair therewith and at an interval therefrom, the second surface having a plurality of second sensor lines (C, D) comprising series of sensor elements (21, 22) extending parallel to respective sensor lines (A, B) of the first surface, with the sensor elements of the respective second sensor lines (C, D) of the second surface being electrically differentially coupled together for supplying a second differential signal, and said electronic device having means for differentially combining the first and second differential signals with respect to the first and second surfaces of said pair, said first surface (e.g. 7b) additionally having a sensor array (E) comprising a plurality of further sensor elements (17) for supplying further signals in accordance with field flux from the field generator (3), the electronic device having means for additively combining said further signals with respect to said sensor array (E), the flux responsive means comprising three pairs of said first and second surfaces, each pair of said first and second surfaces comprising first and second carrier sections (16, 20) having mounted thereon the first and second sensor lines (A, B; C, D) and the further sensor arry (E), the respective pairs of said first and second carrier sections (16, 20) being parallel to respective planes which are perpendicular to one another.

7. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux responsive means for obtaining and evaluating the electrical signals from the flux responsive means, characterized in said field generator (3) being constructed such that it produces a defined irregular field, and said flux responsive means comprising at least one first surface, said first surface having a plurality of sensor elements (17, 18, 19), at least a part of which (18, 19) are arranged to form first sensor lines (A, B) running parallel to each other, the sensor elements of the respective first sensor lines being electrically differentially coupled together for supplying a first differential signal, and comprising at least one second surface disposed parallel to the first surface to form a pair therewith and at an interval therefrom, the second surface having a plurality of second sensor lines (C, D) comprising series of sensor elements (21, 22) extending parallel to respective sensor lines (A, B) of the first surface, with the sensor elements of the respective second sensor lines (C, D) of the second surface being electrically differentially coupled together for suppling a second differential signal, and said electronic device having means for differentially combining the first and second differential signals with respect to the first and second surfaces of said pair, characterized in that, for compensating the earth's magnetic field, said system further comprises compensating arrays (12, 13, 14) of sensor elements rigidly connected in planes parallel to one another and parallel to the planes of the respective pairs (7, 8, 9) of said first and second surfaces.

8. A system according to claim 7, characterized in said system further comprising mounting means (6, 15) carrying three pairs (7, 8, 9) of said first and second surfaces arranged perpendicularly to each other, and having three compensating arrays (12, 13, 14) rigidly connected therewith, with each compensating array being parallel to one of said pairs (7, 8, 9) of said first and second surfaces.

9. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux responsive means for obtaining and evaluating the electrical signals from the flux responsive means, characterized in said field generator (3) being constructed such that it produces a defined irregular field, and said flux responsive means comprising at least one first surface, said first surface having a plurality of sensor elements (17, 18, 19), at least a part of which (18, 19) are arranged to form first sensor lines (A, B) running parallel to each other, the sensor elements of the respective first sensor lines being electrically differentially coupled together for supplying a first differential signal, and comprising at least one second surface disposed parallel to the first surface to form a pair therewith and at an interval therefrom, the second surface having a plurality of second sensor lines (C, D) comprising series of sensor elements (21, 22) extending parallel to respective sensor lines (A, B) of the first surface, with the sensor elements of the respective second sensor lines (C, D) of the second surface being electrically differentially coupled together for supplying a second differential signal, and said electronic device having means for differentially combining the first and second differential signals with respect to the first and second surfaces of said pair, characterized in each of the sensor elements (17 to 22) having a structure of low-remanence magnetic material arranged in superimposed relation thereto.

10. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux responsive means for obtaining and evaluating the electrical signals from the flux responsive means, characterized in said field generator (3) being constructed such that it produces a defined irregular field, and said flux responsive means comprising at least one first surface, said first surface having a plurality of sensor elements (17, 18, 19), at least a part of which (18, 19) are arranged to form first sensor lines (A, B) running parallel to each other, the sensor elements of the respective first sensor lines being electrically differentially coupled together for supplying a first differential signal, and comprising at least one second surface disposed parallel to the first surface to form a pair therewith and at an interval therefrom, the second surface having a plurality of second sensor lines (C, D) comprising series of sensor elements (21, 22) extending parallel to respective sensor lines (A, B) of the first surface, with the sensor elements of the respective second sensor lines (C, D) of the second surface being electrically differentially coupled together for supplying a second differential signal, and said electronic device having means for differentially combining the first and second differential signals with respect to the first and second surfaces of said pair, characterized in that Hall-effect magnetic field sensors are provided as the sensor elements (17 to 22).

11. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux responsive means for obtaining and evaluating the electrical signals from the flux responsive means, characterized in said field generator (3) being constructed such that it produces a defined irregular field, and said flux responsive means comprising at least one first surface, said first surface having a plurality of sensor elements (17, 18, 19), at least a part of which (18, 19) are arranged to form first sensor lines (A, B) running parallel to each other, the sensor elements of the respective first sensor lines being electrically differentially coupled together for supplying a first differential signal, and comprising at least one second surface disposed parallel to the first surface to form a pair therewith and at an interval therefrom, the second surface having a plurality of second sensor lines (C, D) comprising series of sensor elements (21, 22) extending parallel to respective sensor lines (A, B) of the first surface, with the sensor elements of the respective second sensor lines (C, D) of the second surface being electrically differentially coupled together for supplying a second differential signal, and said electronic device having means for differentially combining the first and second differential signals with respect to the first and second surfaces of said pair, characterized in said field generator (3) comprising two magnetic field generator elements (3a, 3b) of similar configuration and each having a first pole of one magnetic polarity and a second pole of the opposite magnetic polarity, and having respective polar axes forming an included angle ($\alpha$) of less than 180° and having the respective first poles of said one magnetic polarity arranged in confronting adjacent relation.

12. A system according to claim 11, characterized in that said two magnetic field generator elements comprise respective bar magnets (3a, 3b).

13. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux respective means for obtaining and evaluating the electrical signals from the flux responsive means, characterized in said field generator (3) being constructed such that it produces a defined irregular field, and said flux responsive means comprising at least one first surface, said first surface having a plurality of sensor elements (17, 18, 19), at least a part of which (18, 19) are arranged to form first sensor lines (A, B) running parallel to each other, the sensor elements of the respective first sensor lines being electrically differentially coupled together for supplying a first differential signal, and comprising at least one second surface disposed parallel to the first surface to form a pair therewith and at an interval therefrom, the second surface having a plurality of second sensor lines (C, D) comprising series of sensor elements (21, 22) extending parallel to respective sensor lines (A, B) of the first surface, with the sensor elements of the respective second sensor lines (C, D) of the second surface being electrically differentially coupled together for supplying a second differential signal, and said electronic device having means for differentially combining the first and second differential signals with respect to the first and second surfaces of said pair, characterized in said system comprising mounting means applicable to the field of dentistry for mounting said flux responsive means, the field generator (3) being adapted to be fixed relative to the lower jaw of the patient.

14. A system according to claim 7 characterized in the system being adapted to be used in the field of dentistry and comprising mounting means for mounting said flux responsive means and comprising a bracket (15) which can be fixed on the head of a patient, said compensating sensor arrays (12, 13, 14) being attached to said bracket (15).

15. A system according to claim 11, characterized in that said system further comprises mounting means (6, 15) carrying three pairs (7, 8, 9) of said first and second surfaces arranged perpendicularly to each other with the three planes defined by the three pairs (7, 8, 9) of said first and second surfaces having a common point of intersection, said mounting means (6, 15) being constructed for fastening on the head of a patient, the field generator being arranged intraorally, and the two magnetic field generator elements, (3a, 3b) thereof having the angle bisector of their included angle (α) extending in the direction of the point of intersection of the three planes.

16. A system for measuring and registering information with respect to location and attitude of a rigid body in space, said system comprising a field generator arranged in fixed relation to the body, flux responsive means for mounting independently of the field generator and at an interval therefrom, and for supplying electrical signals in accordance with field flux from the field generator to represent positional information with respect to the body, and an electronic unit coupled with said flux responsive means for obtaining and evaluating the electrical signals from the flux responsive means, said field generator being constructed such that it produces a defined irregular field, and said flux responsive means comprising at least one first surface, said first surface having a plurality of sensor elements at least a part of which are arranged to form first sensor lines running parallel to each other, the sensor elements of the respective first sensor lines providing respective individual outputs and such respective individual outputs being electrically differentially coupled together for supplying a first differential signal, and comprising at least one second surface disposed between the field generator and the first surface, and parallel to the first surface to form a pair therewith and at an interval therefrom, the second surface having a plurality of second sensor lines comprising series of sensor elements extending parallel to respective sensor lines of the first surface, with the sensor elements of the respective second sensor lines of the second surface providing respective individual outputs and such respective individual outputs being electrically differentially coupled together for supplying a second differential signal, and said electronic device having combining means for differentially combining the first and second differential signals with respect to the first and second surfaces of said pair.

17. A system according to claim 16 with said flux responsive means comprising three pairs of said first and second surfaces (7a, 7b; 8a, 8b; 9a, 9b) arranged in planes perpendicular to one another.

18. A system according to claim 1, with said pair of said first and second surface (e.g. 7a, 7b) comprising a respective pair of first and second plane carrier sections (16, 20) situated opposite and parallel to each other at an interval (d) and mounting the respective first and second sensor lines (A, B; C, D) in such a way that respective ones of the first and second sensor lines (A, C; B, D) of each of the respective pairs of carrier sections (16, 20) are arranged parallel to one another, said flux responsive means comprising three pairs of said first and second surfaces (7a, 7b; 8a, 8b; 9a, 9b) arranged in planes perpendicular to one another.

* * * * *